United States Patent
Cosio et al.

[19]

[11] Patent Number: 5,916,214
[45] Date of Patent: *Jun. 29, 1999

[54] DUAL CURVE ABLATION CATHETER

[75] Inventors: Francisco G. Cosio, Madrid, Spain; Frank Nguyen; Mark A. Maguire, both of San Jose, Calif.

[73] Assignee: Medtronic Cardiorhythm, San Jose, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/825,425

[22] Filed: Mar. 28, 1997

Related U.S. Application Data

[63] Continuation of application No. 08/429,429, May 1, 1995, abandoned.

[51] Int. Cl.⁶ .......................... A61B 17/39; A61B 5/042
[52] U.S. Cl. .......................... 606/41; 600/374; 607/122
[58] Field of Search .................. 606/41, 45, 49; 128/642; 607/122; 600/374

[56] References Cited

U.S. PATENT DOCUMENTS

| | | |
|---|---|---|
| 4,567,901 | 2/1986 | Harris . |
| 4,602,645 | 7/1986 | Barrington et al. . |
| 4,608,986 | 9/1986 | Beranek et al. . |
| 4,784,639 | 11/1988 | Patel . |
| 4,909,787 | 3/1990 | Danforth . |
| 5,058,595 | 10/1991 | Kern . |
| 5,190,050 | 3/1993 | Nitzsche . |
| 5,203,776 | 4/1993 | Durfee . |
| 5,215,540 | 6/1993 | Anderhub . |
| 5,238,005 | 8/1993 | Imran . |
| 5,273,535 | 12/1993 | Edwards et al. . |
| 5,290,229 | 3/1994 | Paskar . |
| 5,299,574 | 4/1994 | Bower . |
| 5,306,262 | 4/1994 | Weldon . |
| 5,306,263 | 4/1994 | Voda . |
| 5,327,889 | 7/1994 | Imran . |
| 5,327,905 | 7/1994 | Avitall . |
| 5,354,297 | 10/1994 | Avitall . |
| 5,358,479 | 10/1994 | Wilson . |
| 5,370,678 | 12/1994 | Edwards et al. . |
| 5,441,483 | 8/1995 | Avitall ....................... 604/95 |

FOREIGN PATENT DOCUMENTS

| | | |
|---|---|---|
| 0 600 676 A3 | 6/1994 | European Pat. Off. . |
| 0 628 322 A3 | 12/1994 | European Pat. Off. . |
| 91/01772 | 2/1991 | WIPO . |
| 94/09843 | 5/1994 | WIPO . |
| WO 94/11057 | 5/1994 | WIPO . |
| 94/24930 | 11/1994 | WIPO . |
| 95/04556 | 2/1995 | WIPO . |

OTHER PUBLICATIONS

B. Olshansky, D.J. Wilber and R.J. Hardiman, "Artrial Flutter–Update on the Mechanism," PACE, vol. 15, pp. 2308–2309, Dec. 1992.

Kaster, "Artrial Flutter," Arrhythmias, pp. 110–114, 1994.

Boaz Avitall, et al., The Anatomical Determinants for the Design of Intracardiac Mapping and Ablation Catheters, PACE vol. 17, May 1994, Part 1, pp. 908–918.

Marketing Brochure (in existence since Jun. 1995) introducting the "Angled Genesis Steerable Catheter," by Electro–Catheter Corporation of Rayway, New Jersey.

*Primary Examiner*—Lee S. Cohen
*Attorney, Agent, or Firm*—Townsend and Townsend and Crew LLP

[57] ABSTRACT

A dual curve ablation catheter (2), especially suited for treating atrial flutter, includes a shaft (4) with a deflectable tip (20) at the distal end (6) and a handle (10) at the proximal end (8). The tip includes a highly flexible distal segment (30), a relatively stiff intermediate segment (28) and a flexible proximal segment (26) so that pulling on a manipulator wire (16) attached to the distal segment causes the distal segment to curve and engage, for example, an isthmus of tissue (106) adjacent the tricuspid valve (104) and the inferior vena cava (98) and causes the proximal segment to curve and press against the wall (110) of the inferior vena cava so to stabilize the catheter. Ablation energy can be supplied through the ablation electrodes (48, 68) simultaneously or one at a time to ablate tissue at the isthmus without the need for moving the catheter.

9 Claims, 7 Drawing Sheets

DUAL CURVE ABLATION CATHETER

CROSS-REFERENCE TO RELATED APPLICATIONS

This is a Continuation of application Ser. No. 08/429,429, filed May 1, 1995, now abandoned, the disclosure of which is incorporated herein by reference.

BACKGROUND OF THE INVENTION

It has long been known that the action of the heart depends upon electrical signals carried along the surface of the heart tissue. Sometimes these electrical signals become faulty. It has been found that ablating (burning) these cardiac conduction pathways in the region of the problem destroys the tissue to eliminate the faulty signal. Electrophysiology (EP) catheters are catheters having one or more electrodes at their tips and are used for both diagnosis and therapy. The electrodes at their tips of EP catheters allow the physician to measure electrical signals along the surface of the heart (called mapping) and then, when necessary, ablate certain tissue using, typically, radio frequency (RF) energy directed to one or more high energy capable ablation electrodes.

SUMMARY OF THE INVENTION

The present invention is directed to an EP ablation catheter especially suited for treating atrial flutter. Atrial flutter is a common rhythm disturbance defined as an atrial tachycardia with atrial rates exceeding 240 beats per minute. The invention creates a linear lesion oriented perpendicularly to the isthmus of tissue between the inferior aspect of the tricuspid valve and the inferior vena cava. The invention ablates a line of tissue across the critical isthmus using ablation-capable electrodes positioned along the tip of the catheter. The catheter is designed to remain in place and provide firm electrode contact during the ablation despite respiratory, cardiac or blood motion during the ablation.

The atrial flutter ablation catheter includes a shaft having proximal and distal ends with a deflectable tip at the distal end and a handle at the proximal end. The tip includes a highly flexible distal segment, a relatively stiff intermediate segment and a flexible proximal segment. Pulling on a manipulator wire, passing through a lumen in the shaft and attached to the distal end the shaft, causes the distal and proximal segments of the tip to curve. When properly positioned for treating atrial flutter, the distal segment engages the isthmus of tissue to be ablated, which lies adjacent the tricuspid valve and the inferior vena cava opening into the right atrium, and the proximal curve segment presses against the wall of the inferior vena cava so as to stabilize the catheter. Ablation energy is supplied through the ablation electrodes, preferably one at a time, to ablate the tissue at the isthmus without the need for moving the catheter once in position.

A rotatable core wire, passing the central lumen and secured to the tip of the shaft, may be used to permit a torquing force to be applied to the distal end of the shaft without rotating the entire catheter. The temperature of the ablation electrodes is preferably monitored, such as using thermocouple wires, to permit enhanced control over the ablation temperatures.

One of the advantages of the invention is that it uses a series of ablation electrodes instead of one long electrode to ablate the cardiac tissue. Making the ablation electrodes electrically isolated from one another and allowing them to be individually powered permits a lower power ablation energy source to be used than would be required if the multiple ablation electrodes were replaced by one long electrode or if the multiple ablation electrodes were all powered simultaneously. Also, multiple electrodes allows bipolar recording to be conducted. Of course, if a power source has sufficient capacity to power more than one ablation electrode, this can be done also.

Other features and advantages of the invention will appear from the following description in which the preferred embodiment has been discussed in detail in conjunction with the accompanying drawings.

DESCRIPTION OF THE PREFERRED EMBODIMENT

Figures 1, 1A:
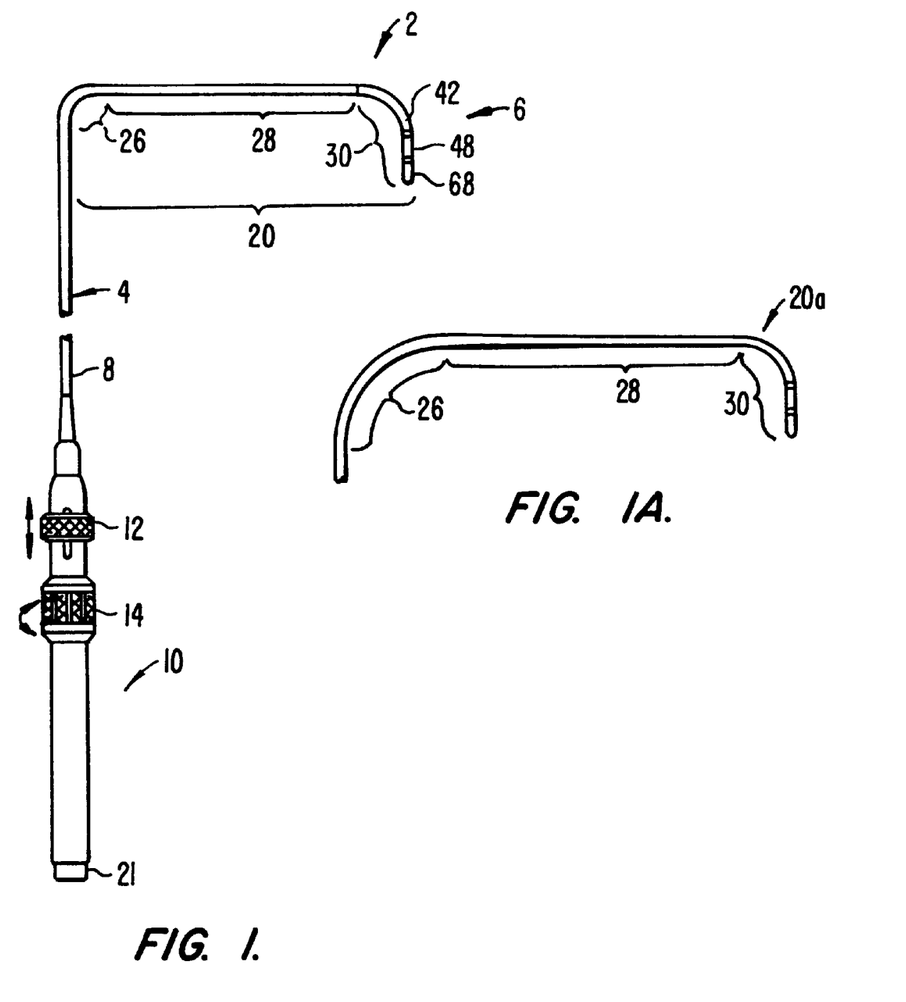
FIG. 1 is an an overall view of an atrial flutter ablation catheter made according to the invention.
FIG. 1A illustrates the tip of the catheter of FIG. 1 in which the proximal segment has a radius of curvature smaller than that of FIG. 1.
Figures 2, 9:
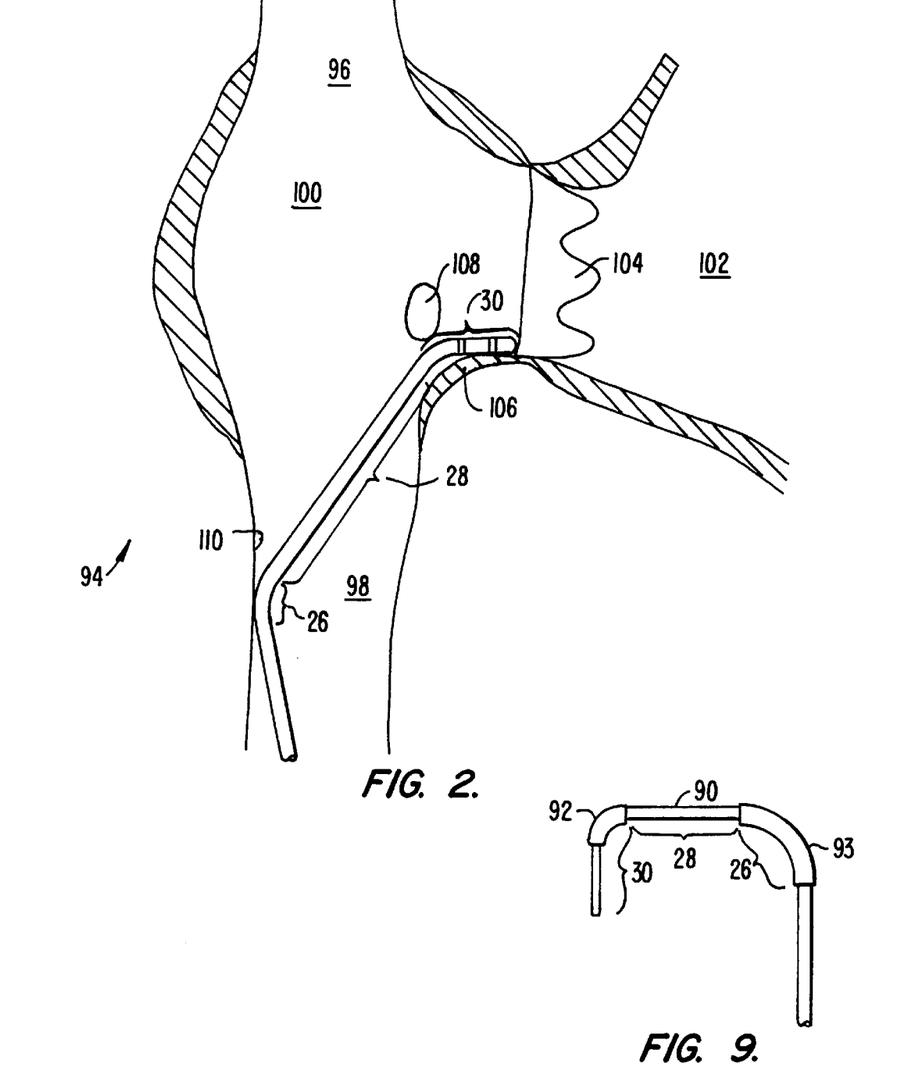
FIG. 2 is a simplified view showing placement of the tip of the cathter of FIG. 1 within the inferior vena cava, right atrium and against the isthmus adjacent the tricuspid valve.
FIG. 9 shows the distal portion of the assembly of FIG. 5 illustrating the positions of the proximal and distal curves relative to the positions of the various tubes mounted over the core wire.

FIG. 1 illustrates an anatomically-conforming dual curve ablation catheter, in particular an atrial flutter ablation catheter 2, including a catheter shaft 4 having a distal end 6 and a proximal end 8. Proximal end 8 is mounted to a handle 10 having an axially slidable manipulator ring 12 and a rotatable lateral deflection ring 14 operably connected to a manipulator wire 16 and a core wire 18, respectively, shown in FIGS. 3A and 3D. Sliding manipulator ring 12 causes a deflectable tip 20 of catheter shaft 4 to deflect as shown in FIGS. 1 and 2 while rotating ring 14 causes lateral deflection of tip 20 through the torquing action of core wire 18.

Handle 10 also includes an electrical connector 21 connected to electrical conductors 22, 23 and thermocouple wires 24, 25. Handle 10 may be of a conventional design, or as shown in U.S. Pat. No. 5,318,525 or in application Ser. No. 08/343,310 filed Nov. 22, 1994, now U.S. Pat. No. 5,845,200, the disclosures of which are incorporated by reference.

Deflectable tip 20 includes three segments, a proximal segment 26, an intermediate segment 28 and a distal segment 30. The construction of distal segment 30 can be seen best with reference to FIGS. 1, 3A–3F, 4, 5 and 9. Shaft 4 at tip 20 is seen to include a 5-lumen shaft body 32 made of Pebax®, a polyamide polyether block copolymer made by Elf Atochem, Inc. of Philadelphia, Pa. To impart more flexibility to this section, the Pebax® material is a relatively lower durometer material, such as 30–40 D. Body 32 includes a central lumen 34 and four satellite lumens 36 extending along the length of body 32. A part of central lumen 34 is occupied by a tubular layer 38 made of polyimide tubing. Core wire 18 fits loosely within central lumen 34 while electrical conductor 22 and thermocouple wires 25 pass through two different satellite lumens 36. The other electrical conductor 23 and thermocouple wires 24 passes through central lumen 34.

Figure 3A:
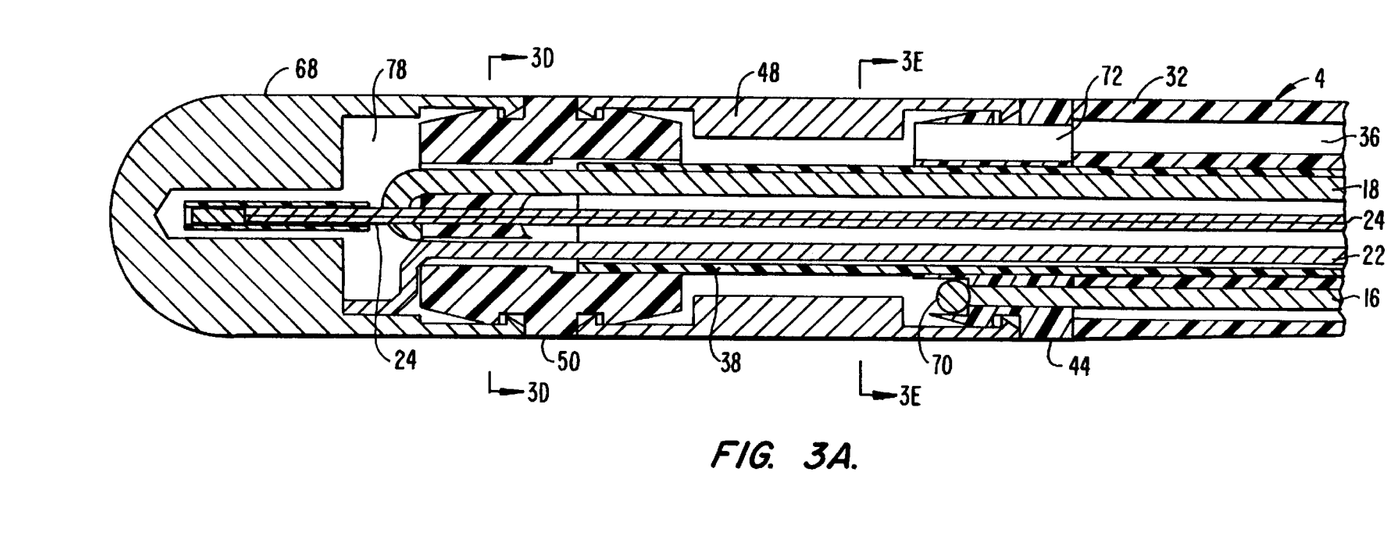
FIGS. 3A and 3B are enlarged cross-sectional views of the tip of the catheter of FIG. 1 omitting the electrical conductor and thermocouple wires passing through the central lumen of the body of the catheter shaft.
Figure 3B:
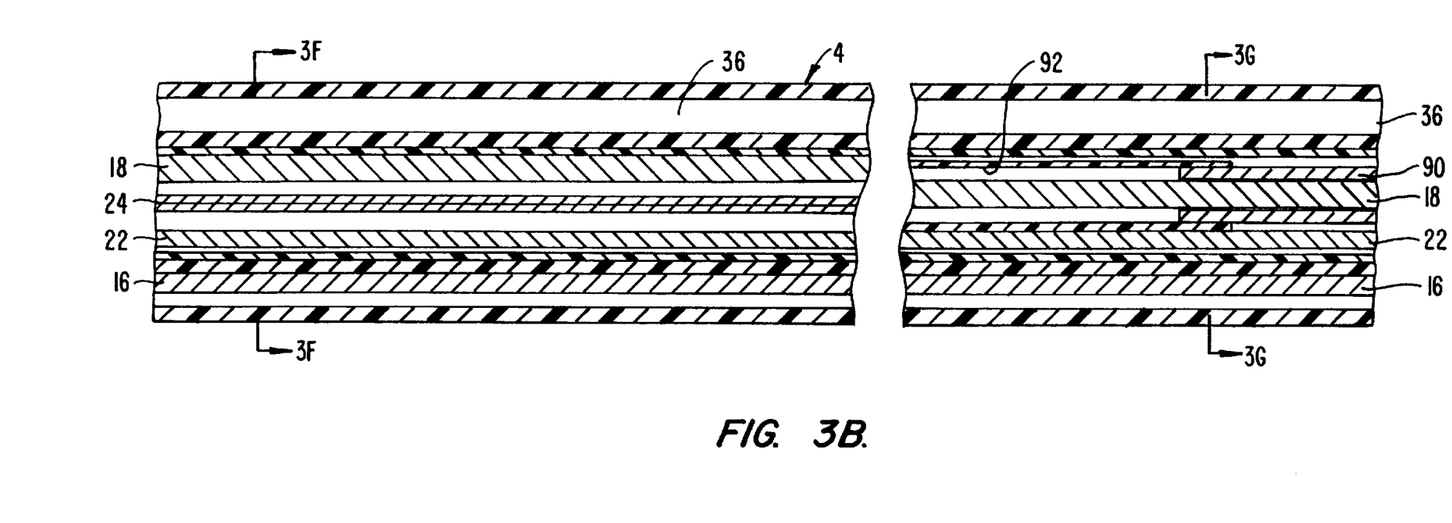
Figure 3C:
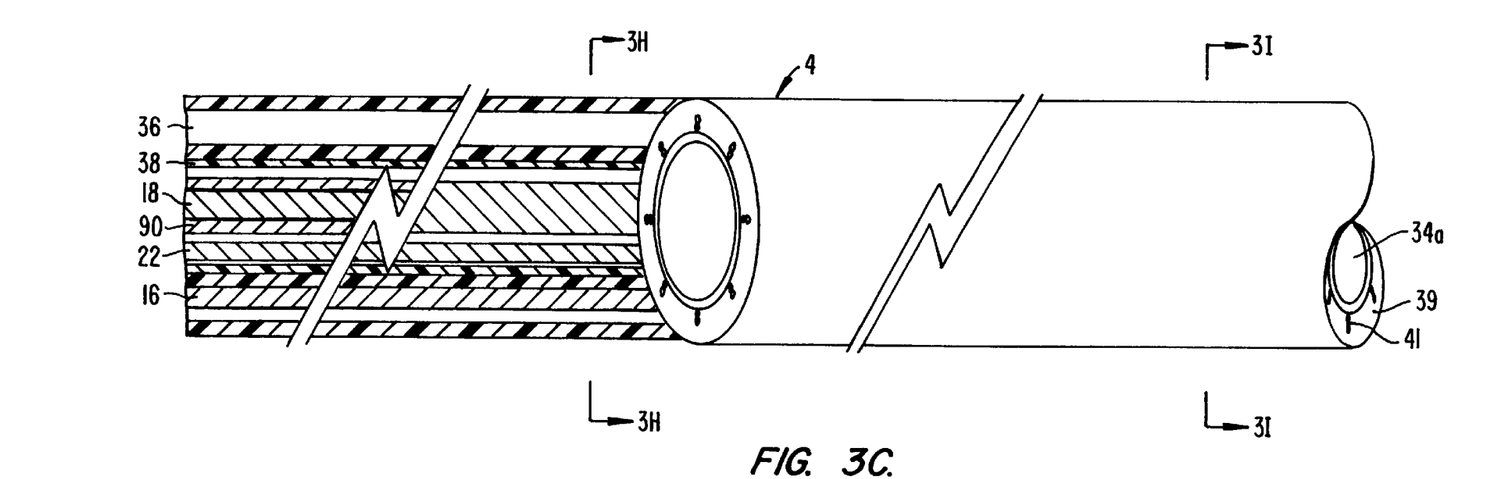
FIG. 3C is an enlarged side view of a segment of the catheter shaft of FIG. 1.
Figure 3D:
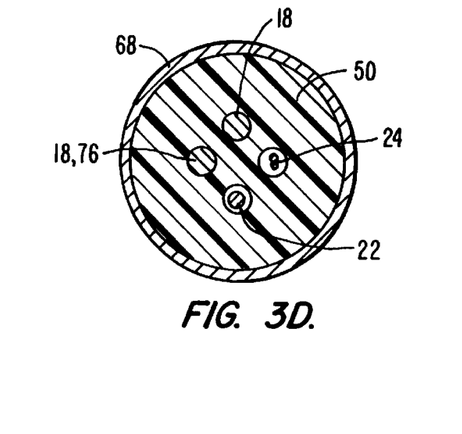
FIGS. 3D–3F are cross-sectional views taken along lines 3D—3D through 3F—3F in FIG. 3A.
Figure 3E:
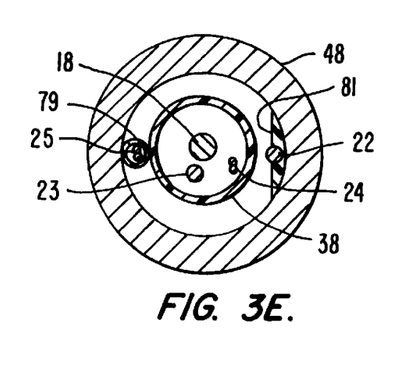
Figure 3F:
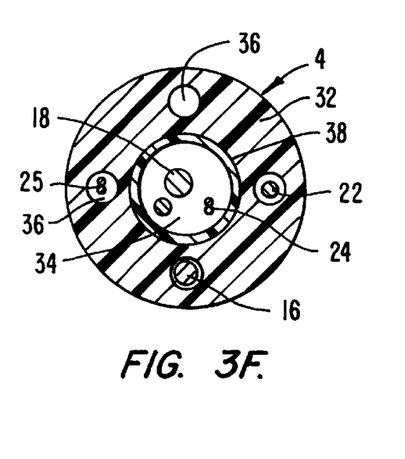
Figure 3G:
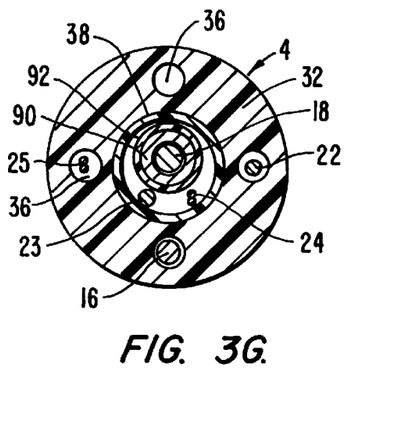
FIGS. 3G and 3H are cross-sectional views taken along lines 3G—3G and 3H—3H in FIG. 3B.
Figure 3H:
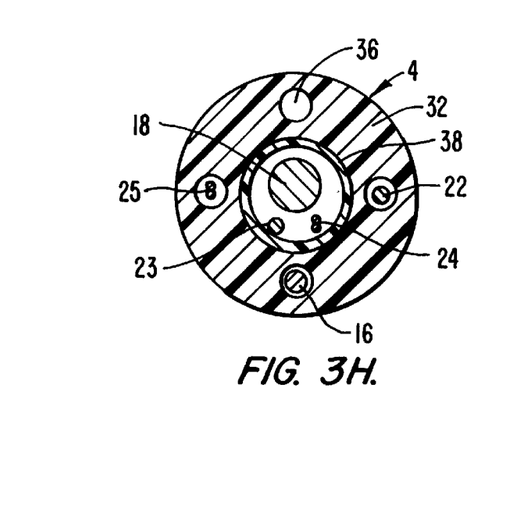
Figure 3I:
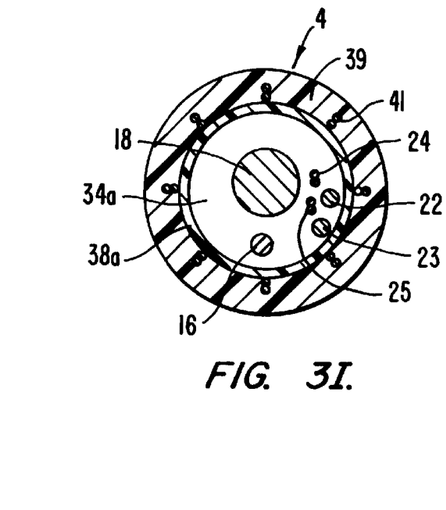
FIG. 3I is a cross-sectional view taken along line 3I—3I in FIG. 3C.

The portion of shaft 4 proximal of deflectable tip 20, see FIGS. 3C and 3I, is relatively stiff to permit controlled placement of tip 20 at the target site as discussed below. Such proximal portion of the shaft 4 includes an outer jacket 39, preferably made of higher durometer Pebax®, such as 55–65 D, reinforced by braided wires 41. A polyimide tubular layer 38a is positioned within the central lumen 34a and houses core wire 18, electrical connectors 22, 23, thermocouple wires 24,25 and manipulator wire 16.

If desired, one or more axially slidable core wires could be used with the distal ends of the core wires positionable at different axial positions along tip 20; doing so would permit the size of the curves of tip 20 to be changed. FIG. 1A illustrates the result of using such a slidable core wire. Tip 20a has a curve at proximal segment 26 with a larger radius than that if FIG. 1; the curves at distal segments 30 are the same for both figures. An example of a catheter with a variable curve tip is described in U.S. patent application Ser. No. 08/343,310 for Steerable Electrophysiology Catheter, the disclosure of which is incorporated by reference.

The distal end 42 of shaft body 32, see FIG. 3A, lies adjacent an insulator 44 made of PEEK (poly-ether-ether-keytone) or other hard, temperature-resistant material. Insulator 44 is bonded to distal end 42 of shaft body 32 by heat fusing and adhesive.

Insulator 44 has five bores or lumens which generally align with the corresponding lumens formed in shaft body 32. A cylindrical ablation electrode 48 is secured to and extends between insulator 44 and a second insulator 50. A tip electrode 68 is secured to the distal end of insulator 50. The connections between electrodes 48, 68 and insulators 44, 50 are preferably through both a snap fit and the use of adhesives or other bonding techniques. Tubular layer 38 terminates at a central bore in insulator 50 and is affixed thereto by adhesive.

Manipulator wire 16 has a ball 70 at its distal end to prevent manipulator wire 16 from being pulled back through one of the bores 72 formed in insulator 44. As seen in FIG. 3D, insulator 50 has four axial bores housing core wire 18, thermocouple wires 24, electrical conductor 22 and the distal end 76 of core wire 18.

It should be noted that in FIGS. 3A and 3B electrical conductor 23 and thermocouple wires 25 are not shown. High power electrical conductors 22, 23 are connected to ablation electrodes 48, 68 in conventional manners, such as soldering or welding. Pairs of thermocouple wires 24, 25 are respectively positioned adjacent ablation electrodes 68, 48 so to permit the temperatures of the ablation electrodes to be monitored. The hollow interior 78 of tip electrode 68 is filled with a thermally conducting but electrically insulating material, such as cyanoacrylate adhesive, so that thermocouple wires 24 positioned within interior 78 will be provided an accurate reading of the temperature of tip electrode 68, without electrical continuity between the two. As shown in FIG. 3E, thermocouple wires 25 and conductor 22 are positioned adjacent electrode 48 by elastically insulating materials 79, 81.

Figure 4:
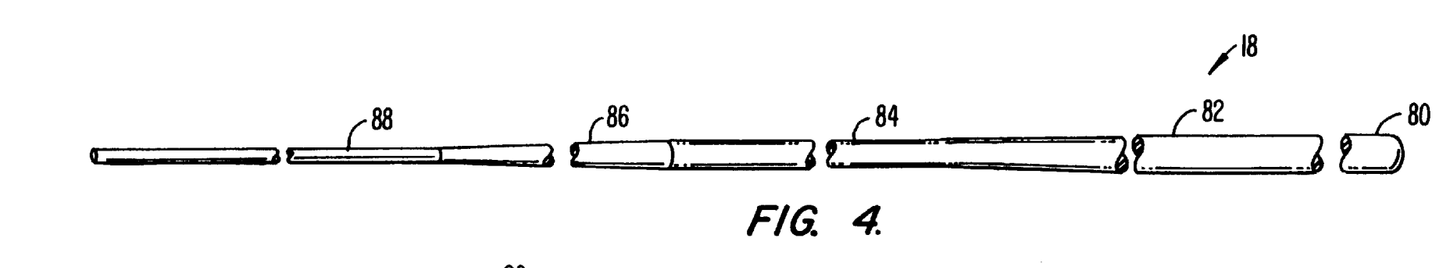
FIG. 4 is a side view showing the tapered nature of the core wire.

Of the proximal, intermediate and distal segments 26, 28, 30, intermediate segment is the stiffest and distal segment 30 is the least stiff while proximal segment 26 has a stiffness somewhat between the two stiffnesses of segments 28, 30. To provide shaft 4 with these three different stiffness for tip 20, core wire 18 is modified to provide these stiffnesses. Core wire 18 is, in one preferred embodiment, about 60 inches (152 cm) long and has five distinct segments. Proximal segment 80 is about 35–39 inches (89 to 99 cm) long and has a diameter of about 0.025 inch (0.64 mm). A second segment 82 tapers in diameter from 0.025 inch to 0.018 inch (0.46 mm) over a distance of about 3 inches (7.6 cm). Third segment 84 is a constant 0.018 inch diameter over a length of about 12–14 inches (30 to 36 cm). These first three segments 80, 82, 84 are all coated with PTFE to minimize friction within shaft 4. The fourth segment 86 core wire 18 tapers from 0.018 inch to 0.0085–0.0095 inch (0.46 mm to 0.22 to 0.24 mm) over a length of 1.5–2.5 inches (3.8 to 6.4 cm) while the final 5-inch (13 cm) length of core wire 18 is a constant diameter fifth segment 88, having a diameter of 0.0085–0.0095 inch.

Figure 5:
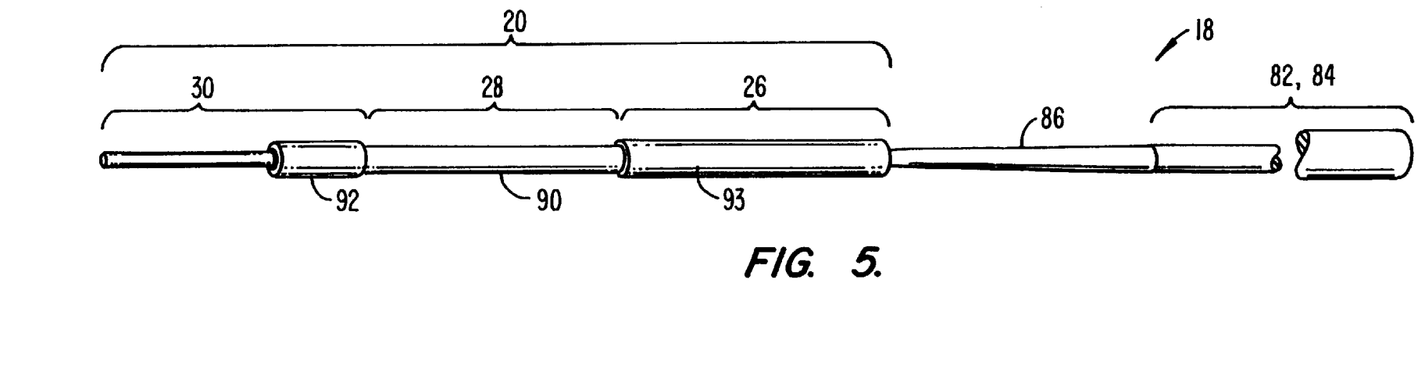
FIG. 5 shows a core wire of FIG. 4 with a hypotube, shown in FIG. 7, and a polyimide tube shown in FIG. 6, strategically positioned along the length of the core wire to provide a very flexible distal segment, a moderately flexible proximal segment and a relatively stiff intermediate segment for the deflectable tip of the catheter of FIG. 1.
Figure 6:
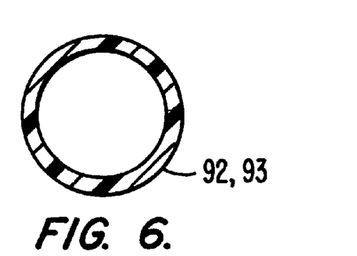
FIGS. 6 and 7 are cross-sectional views of the polyimide tube and hypotube shown in FIG. 5.
Figure 7:
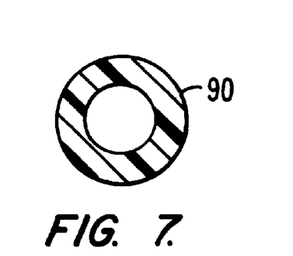

FIGS. 3B, 3G and 5 illustrate how the different stiffnesses for segments 26, 28 and 30 is achieved. A hypotube 90, made of stainless steel, is shown in cross-section in FIG. 7. Hypotube 90 has an inside diameter of 0.010–0.012 inch (0.25 to 0.30 mm) and an outside diameter of 0.018–0.022 inch (0.46 to 0.56 mm) and is used to cover core wire 18 over intermediate segment 28. Hypotube 90 extends for a distance of about 1.0–2.0 inch (2.5–5 cm) in a proximal direction along core wire 18 to ensure that the portion of tip 20 between sections 26 and 30 is relatively stiff. Polyimide tube 92 with an inside diameter of 0.0185–0.0225 inch (0.47 to 0.57 mm) and an outside diameter of 0.024–0.028 inch (0.61 to 0.71 mm) and a length of 0.25–0.5 inch (6.35–12.7 mm) is mounted over hypotube 90 within segment 30. A second polyimide tube 93 with the same I.D. and O.D. as polyimide tube 92 and a length of 1.0–1.5 inch (2.5–3.8 cm) fits over the extension of hypotube 90 within segment 26. In the preferred embodiment, distal segment 30 is about 1.0–2.0 inches (2.54–5.08 cm) long, intermediate segment 28 is about 1.4–2.2 inch (3.5 to 5.5 cm) long and proximal segment 26 is about 0.8–1.6 inches (2.0–4.0 cm) long. Note that hypotube 90 and polyimide tubes 92, 93 are shown only in FIGS. 3B, 3G and 5–7 for simplicity of illustration. The maximum angle for the primary curve at proximal segment 26 is about 120° and for the secondary curve at distal segment 30 is about 100°.

FIG. 9 illustrates how the core wire design matches with the curve shape. In addition to a core wire assembly with sections having different stiffnesses, shaft 4 and intermediate and distal segments 28 and 30 are made having different durometer hardnesses of about 65 D, 55 D and about 30–40 D, respectively.

The use of catheter 2 will be described in conjunction with FIG. 2. FIG. 2 illustrates, in simplified form, a portion of a heart 94 having a superior vena cava 96 and an inferior vena cava 98 opening into a right atrium 100. Also illustrated is a portion of right ventricle 102 separated from right atrium 100 by a tricuspid valve 104. An isthmus of tissue 106 extends between the inferior aspect of tricuspid valve 104 and inferior vena cava 98 adjacent the opening of the coronary sinus 108. Distal segment 30 is sized with an appropriate flexibility so that upon pulling of manipulator wire 16, distal segment 30 assumes the contour generally corresponding to the shape of the coronary tissue at isthmus 106 when oriented perpendicular to the isthmus of tissue 106. Intermediate segment 28 is sufficiently stiff, through the use of both hypotube 90 and polyimide tube 92, so that it remains substantially straight when distal segment 30 is properly flexed. Proximal segment 26 is less stiff than intermediate segment 28 but, in the preferred embodiment, stiffer than distal segment 30 but also has a curve which allows proximal segment 26 of shaft 4 to push against or be braced against the wall 110 of inferior vena cava 98. This stabilizes tip 20 of catheter 2 to help maintain distal segment 30 in the proper position at isthmus of tissue 106.

After any appropriate readings are taken, ablation electrodes 48, 68 are positioned along isthmus of tissue 106. Once in position, electrodes 48, 68 can be coupled to a suitable RF power supply, not shown, through connector 21. One such power supply is shown in U.S. patent application Ser. No. 08/179,558, filed Jan. 10, 1994, now U.S. Pat. No. 5,540,681, the disclosure of which is incorporated by reference. Ablation electrodes 48, 68 are electrically isolated from one another so they can be independently powered from the power supply. This means that the power supply need not be as large as would be required if they were electrically connected to one another or if the separate ablation electrodes were replaced by a single, extra-long ablation electrode. This eliminates the need to move the ablation electrode after each application of power, the "burn-drag-burn" technique used with conventional ablation catheters. Ablation electrodes 48, 68 are powered one-at-a-time.

Figure 10:
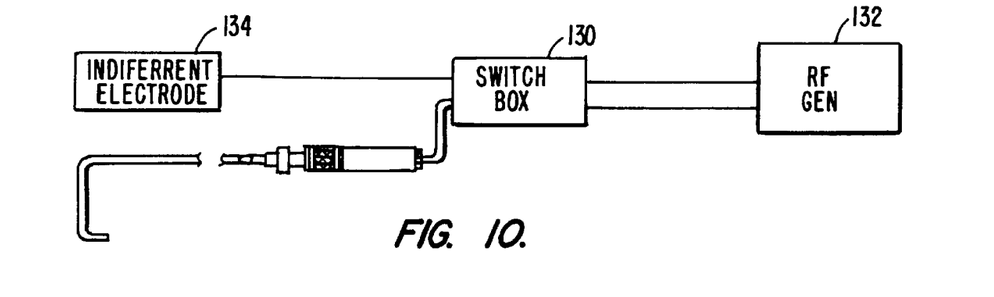
FIG. 10 is a schematic illustration showing the interconnections among the catheter of FIG. 1, a switchbox, an R.F. generator and an indifferent electrode.

Typically, a switchbox 130 is connected between the ablation catheter 2 and an RF generator 132. See FIG. 10. Switchbox 130, which can also be connected to an indifferent electrode 134, allows RF current to be directed to any available ablation electrodes. Thermocouple signals from the particular electrode, used for temperature control, are also supplied to switchbox 130. More than one ablation electrode and thermocouple can be connected simultaneously using switchbox 130. Switchbox 130 can also be automatically controlled.

Figure 8:
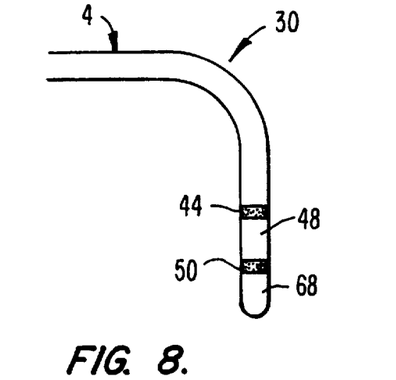
FIG. 8 is an enlarged view of the distal segment of the tip of the cather of FIG. 1.
Figure 8A:
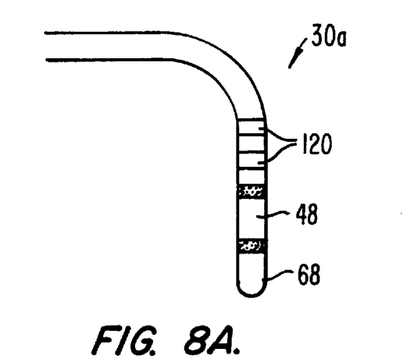
FIGS. 8A–8E are views similar to FIG. 8 of alternative embodiments of the distal segment of the tip of the catheter of FIG. 1.
Figure 8B:
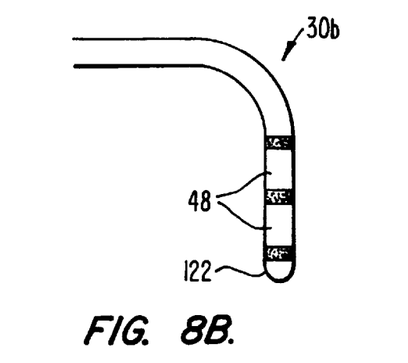
Figure 8C:
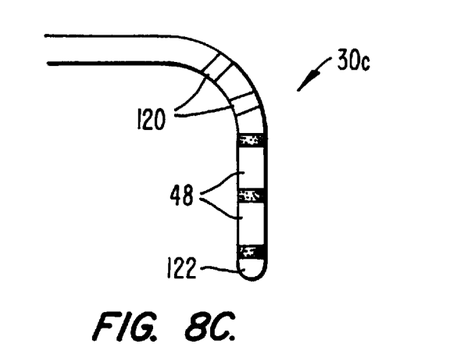
Figure 8D:
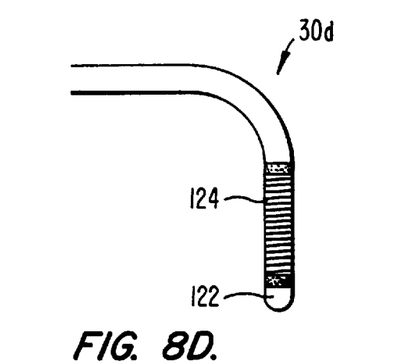
Figure 8E:
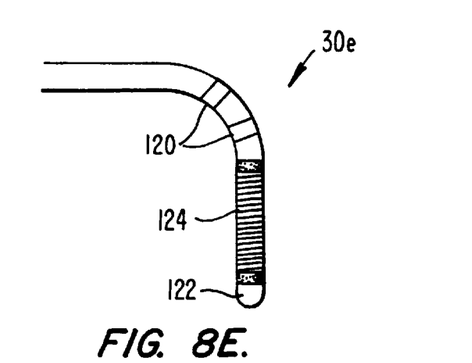

FIGS. 8–8E illustrate various configurations of ablation-capable and mapping electrodes which can be used. FIG. 8 shows ablation-capable electrodes 48, 68, each 4 mm long and having an outside diameter of 0.091 inch (2.3 mm), for catheter 2 of FIGS. 1–7. Distal segment 30a of the embodiment of FIG. 8A is like distal segment 30 of FIG. 8 but has two mapping band electrodes 120. FIG. 8B shows a distal segment 30b with two ablation-capable band electrodes 48 and a half-size (2 mm long) mapping tip electrode 122. Distal segment 30c of FIG. 8C adds two band mapping electrodes 120 to the embodiment of FIG. 8B. The embodiment of FIG. 8D shows the use of a spiral-wound or coiled ablation-capable electrode 124 adjacent to a mapping tip electrode while the FIG. 8E embodiment adds a pair of mapping band electrodes 120 to the FIG. 8D embodiment. Other electrode arrangements are also possible.

Modification and variation can be made to the disclosed embodiment without departing from the subject of the invention as defined in the following claims. For example, materials, diameters and lengths can be changed to suit the particular needs or desires of the user. The attachment and bonding techniques discussed above are merely exemplary; other chemical, mechanical and/or thermal bonding techniques can be used as well. In some cases it may be desired to apply energy to more than one ablation electrode at the same time; for example, four ablation electrodes could be used and powered two-at-a-time. The portion of distal segment 30 carrying ablation-capable electrodes 48 could be made to be curved or curvable if desired. While the invention has its greatest utility as an atrial flutter ablation catheter, it may also find use in ablating tissue at the mitral valve, in addition to tricuspid valve 104, and accessory pathways in the postero-lateral right ventricle. Other curve sizes and spacings for this dual curve catheter could also make it suitable for mapping and ablating other areas of the heart.

What is claimed is:

1. An anatomically-conforming dual curve ablation catheter comprising:
   a shaft having proximal and distal ends with a deflectable tip at the distal end;
   said tip including a curved distal segment, an intermediate segment and a curved proximal segment spaced apart from the distal segment by the intermediate segment;
   at least one ablation-capable electrode positioned along at least the distal segment of the deflectable tip;
   a handle at the proximal end of the shaft;
   an ablation energy conductor extending along the shaft between each of said at least one ablation-capable electrode and the handle;
   the distal, proximal and intermediate segments have first, second and third stiffnesses, said third stiffness being substantially greater than the second stiffness and the second stiffness being at least as stiff as the first stiffness;
   a movable tip deflector device mounted to the handle; and
   an axially movable manipulator wire coupling the distal end to the tip deflector device so that movement of the tip deflector device causes the manipulator wire to pull on said distal end causing said distal and proximal curved segments to bend to a first chosen shape, to be conformingly engageable with an ablation target site, and to a second chosen shape, respectively, while said intermediate segment is sufficiently stiff so to remain substantially straight.

2. The catheter according to claim 1 wherein the second stiffness is greater than the first stiffness.

3. An atrial flutter ablation catheter comprising:
   a shaft having proximal and distal ends with a deflectable tip at the distal end;
   said tip including a distal segment, an intermediate segment and a proximal segment spaced apart from the distal segment by the intermediate segment;
   ablation-capable, electrically isolated electrodes positioned along at least the distal segment of the deflectable tip, said electrodes including a tip electrode;

a handle at the proximal end of the shaft;

a movable tip deflector device mounted to the handle;

an axially movable manipulator wire coupling the distal end to the tip deflector device so that movement of the tip deflector device causes the manipulator wire to pull on said distal end causing said distal and proximal segments to bend to first and second chosen shapes while said intermediate segment is sufficiently stiff so to remain substantially straight;

conductors extending along the shaft between the ablation-capable electrodes and the handle;

the distal segment with said first chosen shape conformingly engageable with an isthmus of tissue adjacent a tricuspid valve and an inferior vena cava opening into a right atrium; and the proximal segment with said second chosen shape pressable against a wall of the inferior vena cava so to stabilize the catheter while ablation energy is deliverable to the isthmus of tissue through said ablation-capable electrodes.

4. The catheter according to claim 3 further comprising a temperature sensor associated with at least one of said ablation-capable electrodes.

5. The catheter according to claim 3 further comprising at least one mapping electrode along the distal segment.

6. An atrial flutter ablation catheter comprising:

a shaft having proximal and distal ends with a deflectable tip at the distal end;

said tip including a distal segment, an intermediate segment and a proximal segment spaced apart from the distal segment by the intermediate segment;

the distal, proximal and intermediate segments having first, second and third stiffnesses, said third stiffness being substantially greater than the second stiffness and the second stiffness being at least as stiff as the first stiffness;

a series of ablation-capable, electrically isolated electrodes positioned along at least the distal segment of the deflectable tip, said electrodes including a tip electrode and a series of circumferential electrodes circumscribing the shaft;

a handle at the proximal end of the shaft;

a movable tip deflector device mounted to the handle;

an axially movable manipulator wire coupling the distal end to the tip deflector device so that movement of the tip deflector device causes the manipulator wire to pull on said distal end causing said distal and proximal segments to bend to first and second chosen shapes while said intermediate segment is sufficiently stiff so to remain substantially straight;

ablation energy conductors extending along the shaft between the ablation-capable electrodes and the handle;

at least one mapping electrode along the distal segment electrically coupled to the handle;

the distal segment with said first chosen shape conformingly engageable with an isthmus of tissue adjacent a tricuspid valve and an inferior vena cava opening into a right atrium; and the proximal segment with said second chosen shape pressable against a wall of the inferior vena cava so to stabilize the catheter while ablation energy is deliverable to the isthmus of tissue through said ablation-capable electrodes.

7. The catheter according to claim 6 further comprising a temperature sensor associated with at least one of said ablation-capable electrodes.

8. An anatomically-conforming dual curve catheter comprising:

a shaft having proximal and distal ends with a deflectable tip at the distal end;

said tip including a bendable distal segment, an intermediate segment and a bendable proximal segment spaced apart from the distal segment by the intermediate segment;

at least one electrode positioned on the deflectable tip;

a handle at the proximal end of the shaft;

an energy conductor extending along the shaft between said at least one electrode and the handle;

the distal, proximal and intermediate segments having first, second and third stiffnesses, said third stiffness being substantially greater than the second stiffness and the second stiffness being at least as stiff as the first stiffness;

a movable tip deflector device mounted to the handle; and an axially movable manipulator wire coupling the distal end to the tip deflector device so that movement of the tip deflector device causes the manipulator wire to pull on said distal end causing said distal and proximal segments to bend to a first chosen shape, to be conformingly engageable with a target site, and to a second chosen shape, respectively, while said intermediate segment is sufficiently stiff so to remain substantially straight.

9. An anatomically-conforming dual curve catheter comprising:

a shaft having proximal and distal ends with a deflectable tip at the distal end;

said tip including a bendable distal segment, an intermediate segment and a bendable proximal segment spaced apart from the distal segment by the intermediate segment;

means, actuatable from the proximal end of the shaft, for forming first and second curves along said distal and proximal segments so a part of said deflectable tip is generally conformingly engageable with a target site;

at least one electrode positioned along at least one of the intermediate and distal segments of the deflectable tip;

a handle at the proximal end of the shaft;

an energy conductor extending along the shaft between said at least one electrode and the handle;

the distal segment having a first chosen shape, said distal segment conforming with an isthmus of tissue, located adjacent a tricuspid valve and an inferior vena cava opening into a right atrium, as the target site; and the proximal segment having a second chosen shape, said proximal segment positioned to be pressable against a wall of the inferior vena cava so to stabilize the catheter while ablation energy is delivered to the isthmus of tissue through said at least one electrode.

* * * * *